(12) United States Patent
Lehtonen

(10) Patent No.: US 8,567,267 B2
(45) Date of Patent: Oct. 29, 2013

(54) METHOD AND DEVICE FOR CUTTING OFF ONE OR MORE SAMPLE REGIONS FROM A SAMPLE CARRIER

(75) Inventor: Jussi Petteri Lehtonen, Turku (FI)

(73) Assignee: Wallac Oy, Turku (FI)

( * ) Notice: Subject to any disclaimer, the term of this patent is extended or adjusted under 35 U.S.C. 154(b) by 206 days.

(21) Appl. No.: 13/295,439

(22) Filed: Nov. 14, 2011

(65) Prior Publication Data
US 2012/0186368 A1 Jul. 26, 2012

Related U.S. Application Data

(60) Provisional application No. 61/434,937, filed on Jan. 21, 2011.

(30) Foreign Application Priority Data

Jan. 21, 2011 (FI) ..................................... 20115058

(51) Int. Cl.
*G01N 1/04* (2006.01)
(52) U.S. Cl.
USPC ..................................................... 73/864.41
(58) Field of Classification Search
None
See application file for complete search history.

(56) References Cited

U.S. PATENT DOCUMENTS

| 2004/0074410 | A1 | 4/2004 | Domes |
| 2004/0146434 | A1 | 7/2004 | Kane et al. |
| 2009/0078717 | A1 * | 3/2009 | Kowari et al. ..................... 221/1 |
| 2010/0182728 | A1 | 7/2010 | Jendrejack et al. |

FOREIGN PATENT DOCUMENTS

| EP | 0 213 690 A2 | 3/1987 |
| EP | 1155834 A2 | 11/2001 |
| JP | 2008304235 A | 12/2008 |
| WO | 2009/130378 A1 | 10/2009 |

OTHER PUBLICATIONS

Finnish search report, dated Sep. 21, 2011, from corresponding Finnish application.
Extended European Search Report, dated Dec. 12, 2012, from EP application.

* cited by examiner

*Primary Examiner* — Robert R Raevis
(74) *Attorney, Agent, or Firm* — Young & Thompson

(57) ABSTRACT

A device for cutting off one or more sample regions from a sample carrier that contains impregnated sample material, e.g. blood, is described. The device comprises: a cutting unit (101) for cutting off the one or more sample regions from the sample carrier, a support element (102) for supporting a sample well element (117) so that a sample well of the sample well element is able to receive each sample region cut off from the sample carrier, and an ionizer (103) for ionizing gas, e.g. air, that is, when the sample well element has been placed to the support element, in contact with the sample well element so as to discharge possible static electricity from the sample well element with the aid of the ionized gas. Therefore, the adverse effect of static electricity that can be present in the sample well element can be reduced or eliminated.

27 Claims, 4 Drawing Sheets

METHOD AND DEVICE FOR CUTTING OFF ONE OR MORE SAMPLE REGIONS FROM A SAMPLE CARRIER

FIELD OF THE INVENTION

The invention relates to a method and a device for cutting off one or more sample regions from a sample carrier that contains impregnated sample material, e.g. dried blood.

BACKGROUND

A conventional practice is to impregnate one or more drops of fluid to be examined onto a sample carrier, dry the sample carrier impregnated with the fluid, and then send the sample carrier to a laboratory for examination. The fluid to be examined can be, for example, blood of a newborn baby and the sample carrier can be, for example, a sheet of filter paper or some other suitable porous material which is able to absorb the fluid to be examined. In the laboratory, one or more regions containing the fluid to be examined, i.e. one or more sample regions, are cut off from the sample carrier and the one or more pieces that have been cut off are conveyed, for further analysis, to one or more sample wells of e.g. a microtitration plate or some other sample well element. Each sample region can be cut off from the sample carrier for example with a punch and a die provided with a channel for the punch, where the punch is arranged to cut off the sample region with a single stroke through the sample carrier. It is also possible to use a cutting instrument capable of producing a localized, point-form cut on the sample carrier and to move the point-form cutting impact produced by the cutting instrument along the outer periphery of each sample region so as to detach the sample region from the sample carrier. The sample well element, e.g. a microtitration plate, can get charged with static electricity when it is handled and it is placed to a device for cutting off the one or more sample regions from the sample carrier. The sample well element can get electrically charged for example when it is removed from its package in the laboratory. The static electricity makes it more challenging to convey the sample regions cut off from the sample carrier to right sample wells of the sample well element because the electrically charged sample well element creates in its surroundings a non-homogenous electrical field that may polarize the sample regions, i.e. the detached pieces of the sample carrier material, and thus electrical forces may be directed to the sample regions.

A device according to the prior art for cutting off one or more sample regions from a sample carrier comprises, in addition to a cutting unit for cutting off the sample regions, means for humidifying air and blowing the humidified air to the surroundings of the sample well element in order to discharge possible static electricity from appropriate parts of the device and/or from the sample regions with the aid of the water carried by the humidified air. In some situations it might be, however, challenging to control the air humidity so that undesirable condensation of water to structures of the device is sufficiently low but, on the other hand, the discharging of the static electricity is effective enough.

SUMMARY

The following presents a simplified summary in order to provide a basic understanding of some aspects of various invention embodiments. The summary is not an extensive overview of the invention. It is neither intended to identify key or critical elements of the invention nor to delineate the scope of the invention. The following summary merely presents some concepts of the invention in a simplified form as a prelude to a more detailed description of exemplifying embodiments of the invention.

In accordance with the first aspect of the invention, there is provided a new device for cutting off one or more sample regions from a sample carrier that contains impregnated sample material, e.g. blood. The device according to the invention comprises:
 a cutting unit for cutting off the one or more sample regions from the sample carrier,
 a support element for supporting a sample well element so that the sample well element is able to receive the one or more sample regions cut off from the sample carrier, and
 an ionizer for ionizing gas, e.g. air, that is, when the sample well element has been placed to the support element, in contact with the sample well element so as to discharge static electricity from the sample well element with the aid of the ionized gas.

In conjunction with the above-described device, there are no such challenges as when using humidified air for discharging static electricity from the sample well element.

In accordance with the second aspect of the invention, there is provided a new method for cutting off one or more sample regions from a sample carrier that contains impregnated sample material. The method according to the invention comprises:
 ionizing gas, e.g. air, that is in contact with a sample well element using an electrically charged ionizer in order to discharge static electricity from the sample well element with the aid of the ionized gas.
 cutting off the one or more sample regions from the sample carrier, and
 receiving the one or more sample regions cut off from the sample carrier at one or more sample wells of the sample well element.

A number of exemplifying embodiments of the invention are described in accompanied dependent claims.

Various exemplifying embodiments of the invention both as to constructions and to methods of operation, together with additional objects and advantages thereof, will be best understood from the following description of specific exemplifying embodiments when read in connection with the accompanying drawings.

The verbs "to comprise" and "to include" are used in this document as open limitations that neither exclude nor require the existence of unrecited features. The features recited in depending claims are mutually freely combinable unless otherwise explicitly stated.

BRIEF DESCRIPTION OF THE FIGURES

The exemplifying embodiments of the invention and their advantages are explained in greater detail below in the sense of examples and with reference to the accompanying drawings, in which.

DESCRIPTION OF THE EMBODIMENTS

Figure 1A:
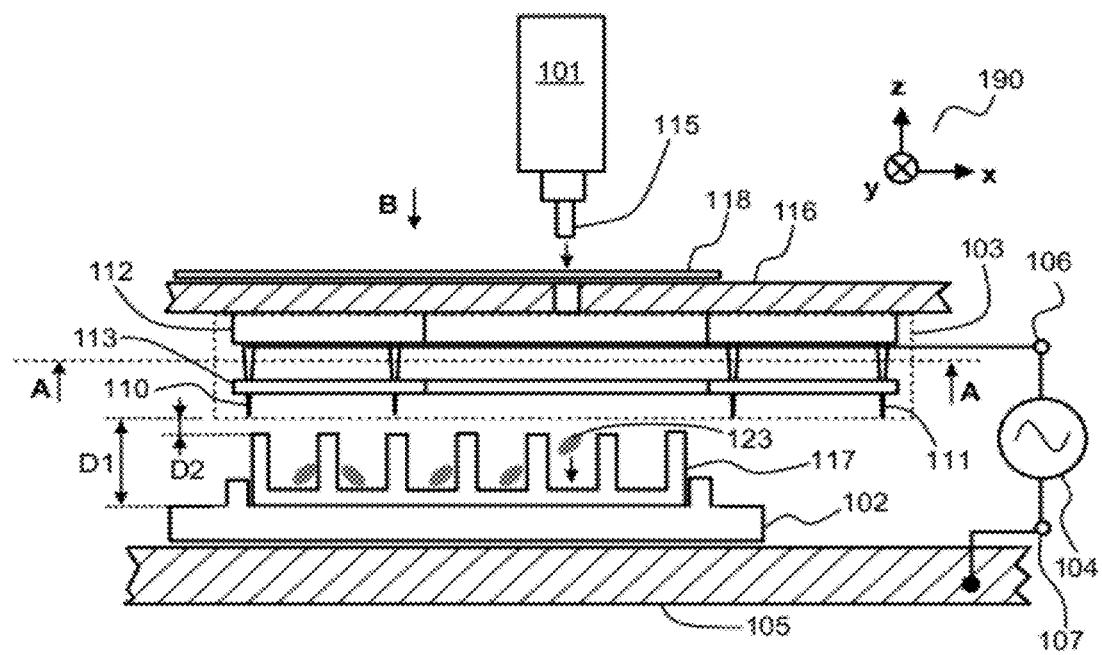
FIG. 1a shows a schematic side view of a device according to an exemplifying embodiment of the invention for cutting off one or more sample regions from a sample carrier that contains impregnated sample material, e.g. blood.
Figure 1B:
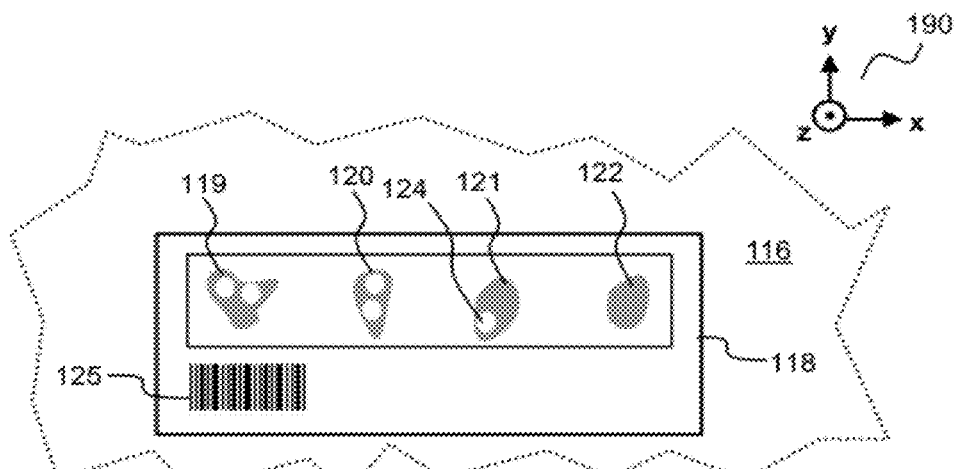
FIG. 1b shows a view seen along the arrow B presented in FIG. 1a, FIG. 1c shows a section taken along the line A-A presented in FIG. 1a, FIG. 2 shows a section view of an ionizer of a device according to another embodiment of the invention for cutting off one or more sample regions from a sample carrier that contains impregnated sample material.

FIG. 1a shows a schematic side view of a device according to an exemplifying embodiment of the invention for cutting off one or more sample regions from a sample carrier 118 that contains impregnated sample material. FIG. 1b shows a view seen along the arrow B presented in FIG. 1a. The sample carrier 118 may comprise, for example, a sheet of filter paper or some other suitable porous material which is able to absorb the sample material that can be e.g. blood of a newborn baby. Blotches 119, 120, 121 and 122, see FIG. 1b, on the sample carrier 118 are the regions of the sample carrier into which the sample material has been impregnated. Sample regions are cut off from the regions of the sample carrier into which the sample material has been impregnated. After cutting, the detached sample regions are conveyed for further analysis to sample wells of a sample well element 117 that can be e.g. a microtitration plate. For example, a detached sample region 123 shown in FIG. 1a has been cut off from the region 121 shown in FIG. 1b. The region 121 has a hole 124 on the place from which the sample region 123 has been cut off. The detached sample region 123 that has been received at the sample well may be later subjected to e.g. biochemical analysis. The sample carrier 118 may comprise a machine-readable identifier element 125 that may contain, for example, information about the donor of the sample material, information about the time and place of taking the sample, and/or other appropriate information.

The device for cutting off the one or more sample regions from the sample carrier comprises a cutting unit 101 for cutting off the sample regions from desired locations of the sample carrier. In the exemplifying case shown in FIG. 1, the cutting unit comprises a punch 115 and a die 116 provided with a channel for the punch. The punch is arranged to detach each sample region from the sample carrier 118 with a stroke through the sample carrier. Mechanical support structures which support the cutting unit 101 are not shown in FIG. 1a, but the mechanical support structures including possible servomotors and/or position sensors can be such as known from the prior art. In a device according to another embodiment of the invention, the cutting unit comprises a cutting instrument for producing a localized, point-form cut on the sample carrier and equipment for directing the cutting instrument so that the cutting impact produced by the cutting instrument is moved along the outer periphery of each sample region so as to cut off the sample region from the sample carrier. The above-mentioned cutting instrument can be, for example, a laser beam cutter or a liquid, e.g. water, jet cutter.

The device comprises a support element 102 for supporting the sample well element 117 so that a sample well of the sample well element is able to receive each sample region cut off from the sample carrier. The support element 102 is preferably connected to mechanical support structures which are capable of moving the support element in the xy-plane of a coordinate system 190. The above-mentioned mechanical support structures are not shown in FIG. 1a, but the mechanical support structures including possible servomotors and/or position sensors can be such as known from the prior art.

Figure 1C:
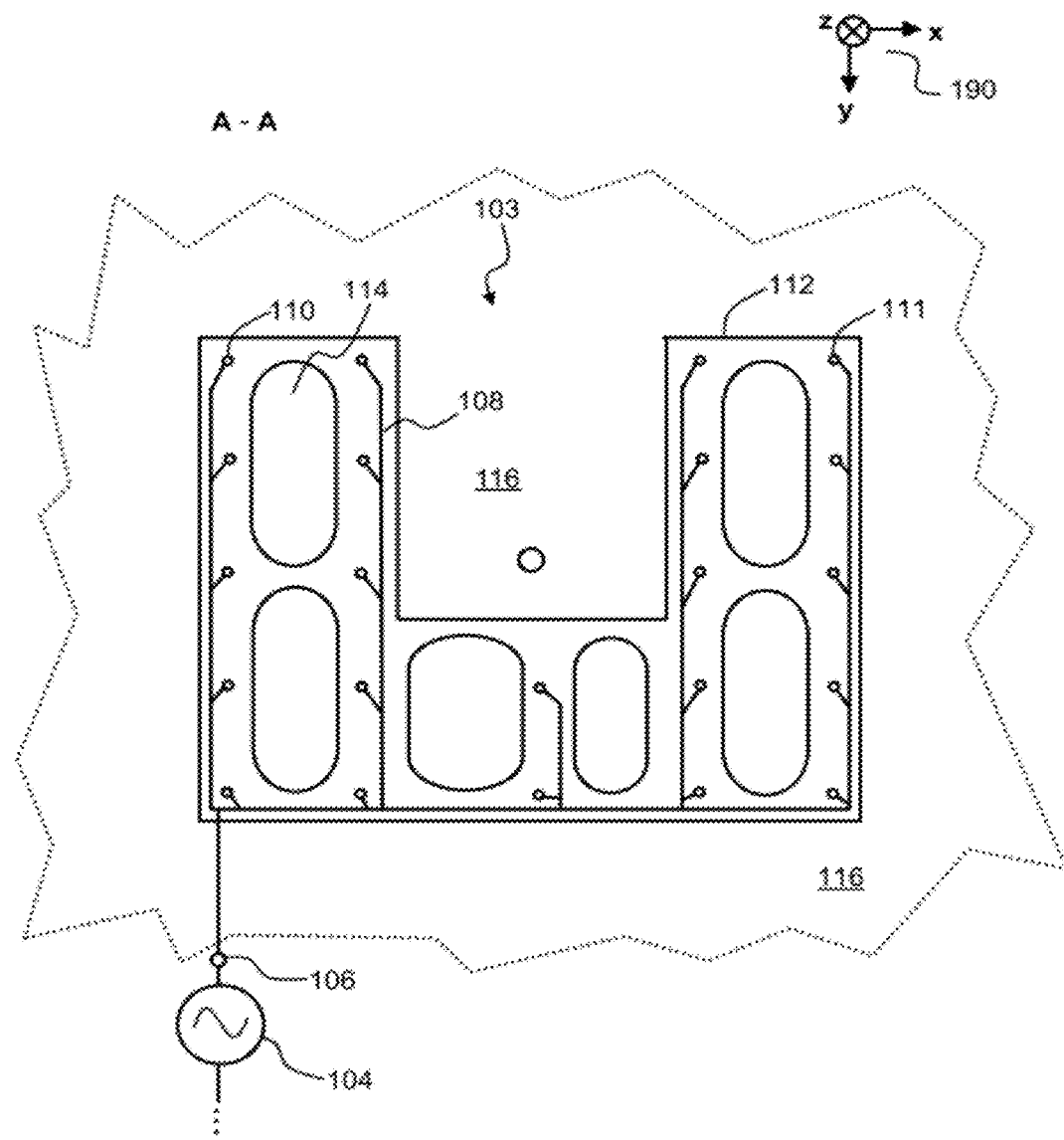

The device comprises an ionizer 103 for ionizing gas that is, when the sample well element 117 has been placed to the support element 102, in contact with the sample well element so as to discharge static electricity from the sample well element with the aid of the ionized gas. The gas is typically, but not necessarily, air. FIG. 1c shows a section A-A of the ionizer 103. In the exemplifying case illustrated in FIGS. 1a-1c, the ionizer comprises a plurality of sharpened metallic spikes, such as spikes 110 and 111, so as to maximize the peak value of electrical field strength V/m in the vicinity of the ionizer. The spikes are mechanically supported with a support that is made of electrically non-conducting material such as for example plastics. The support comprises two parts 112 and 113 so that the part 112 supports the butt ends of the spikes and the part 113 supports the tip ends of the spikes. As can be seen form FIG. 1c, the spikes are connected via thin electrical conductors, such as an electrical conductor 108, to a first terminal 106 of a voltage source 104. In the exemplifying case illustrated in FIGS. 1a-1c, the voltage source 104 is an alternating "AC" voltage source, and a second electrical terminal of the voltage source is connected to a body 105 of the device. The frequency of alternating voltage produced by the voltage source 104 can be for example on the range 20-200 Hz, and the amplitude of the alternating voltage can be for example on the range 2-10 kV. More advantageously, the amplitude of the alternating voltage can be on the range 5-10 kV. The high electrical field strength in the vicinity of the tips of the spikes ionizes air, or other gas, and the ionized air in turn neutralizes possible electrical charge from the sample well element 117. By using the alternating voltage that changes its polarity periodically, the above-mentioned neutralization can be arranged to take place regardless of the polarity of the possible electrical charge in the sample well element.

The structure of the ionizer such that there are thin spikes which are connected to the voltage source 104 with thin electrical conductors and which are mechanically supported with electrically non-conductive support is advantageous in the respect that the capacitance of the ionizer with respect to other parts, e.g. the body, of the device is minimized. The capacitance of the ionizer with respect to the body should be small in order to minimize capacitive current through the ionizer. The capacitive current causes undesirable voltage loss because the internal impedance of the voltage source 104 has to be relatively high due to safety issues. The resistive part of the internal impedance of the voltage source 104 may have to be even mega-ohms and thus even a relatively small current may cause an inconveniently high voltage loss. In more general terms, the capacitance between the ionizer and the other parts of the device can be made small by minimizing the total area of the electrical conductors of the ionizer and by placing the electrical conductors a distance apart from the other parts. This can be achieved, for example so that the ionizer comprises elongated electrical conductors supported by a support made of electrically non-conductive material so that the total area of the electrical conductors is significantly, e.g. at least ten times, smaller than the area of a smallest closed spatial surface capable of enclosing the ionizer.

The surface of support 112, 113 may get in some situations somewhat electrically conductive because of water that may condense on the surface of the support. Therefore, the support is advantageously provided with holes and/or cuts in order to decrease the surface area of the support so as to minimize the capacitance between the support and other parts of the device. FIG. 1c illustrates how the part 112 of the support can comprise holes, such as a hole 114, for decreasing its surface area.

In the exemplifying case illustrated in FIGS. 1a-1c, the spikes of the ionizer are directed so that, when the sample well element 117 is in its normal operation position in the support element 102, the spikes are towards openings of the sample wells of the sample well element. A distance D1, see FIG. 1a, from tips of the spikes to a spatial plane that co-insides with a bottom of the sample well element 117, when the sample well element is in its normal operation position in the support element, can be on the range 10-15 mm. Thus, if the height of the sample well element 117 is about e.g. 9 mm, the distance D2 from tips of the spikes to the openings of the sample wells is on the range 1-6 mm.

It should be noted that the ionizer with the spikes is not the only possible choice. The ionizer could also comprise one or more wires which are arranged to form e.g. closed wire loops and which are so thin that a sufficient electrical field strength V/m is achieved at the surfaces of the said wires.

Furthermore, it should be noted that the device may comprise the voltage source 104 as a part of the device and/or the device may comprise electrical connectors for connecting to an external voltage source.

Figure 2:
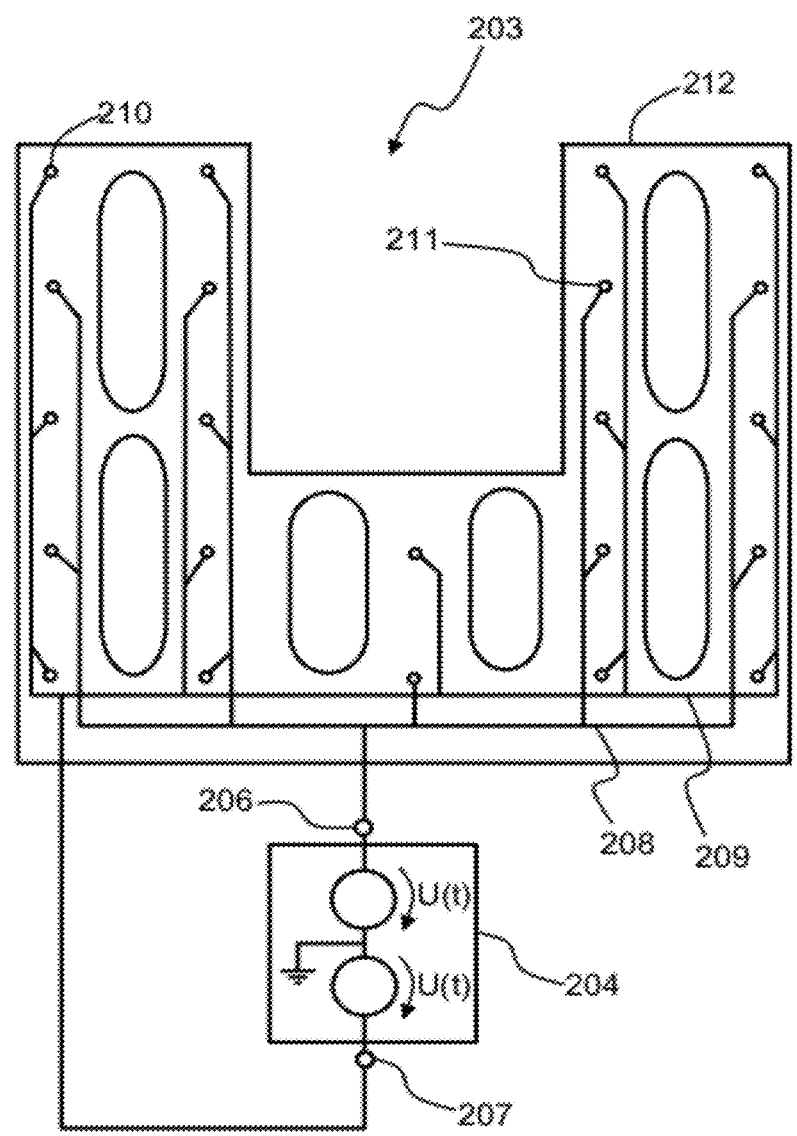

FIG. 2 shows a section view of an ionizer 203 of a device according to another embodiment of the invention for cutting off one or more sample regions from a sample carrier that contains impregnated sample material, e.g. blood. The section shown in FIG. 2 is taken in the same way as the section shown in FIG. 1c. The ionizer 203 comprises two parts that are electrically insulated from each other. The first part of the ionizer comprises, among others, a spike 211 and an electrical conductor 208 that is arranged to electrically connect the spikes of the first part to each other. The second part of the ionizer comprises, among others, a spike 210 and an electrical conductor 209 that is arranged to electrically connect the spikes of the second part to each other. The first part of the ionizer is connected to a first electrical terminal 206 of a voltage source 204, and the second part of the ionizer is connected to a second electrical terminal 207 of the voltage source 204. The voltage source is arranged to produce symmetrical voltage±U(t) with respect to ground, e.g. a body of the device, in order to prevent uncontrolled floating of the potential of the ionizer. The use of the differential voltage as illustrated in FIG. 2 results in that the ionizer can have simultaneously both positively charged peaks and negatively charged peaks. Hence, the voltage source 204 can be either an alternating "AC" voltage source or a direct "DC" voltage source. The voltage source 204 may comprise a transformer a middle point of a secondary winding of which has been grounded. In a case the voltage 2×U(t) produced by the voltage source 204 is AC-voltage, the frequency can be on the range 20-200 Hz, and the amplitude can be on the range 2-10 kV, or more advantageously on the range 5-10 kV. In a case the voltage 2×U(t) is DC-voltage, the value of the DC-voltage can be on the range 2-10 kV, or more advantageously on the range 5-10 kV.

Figure 3:
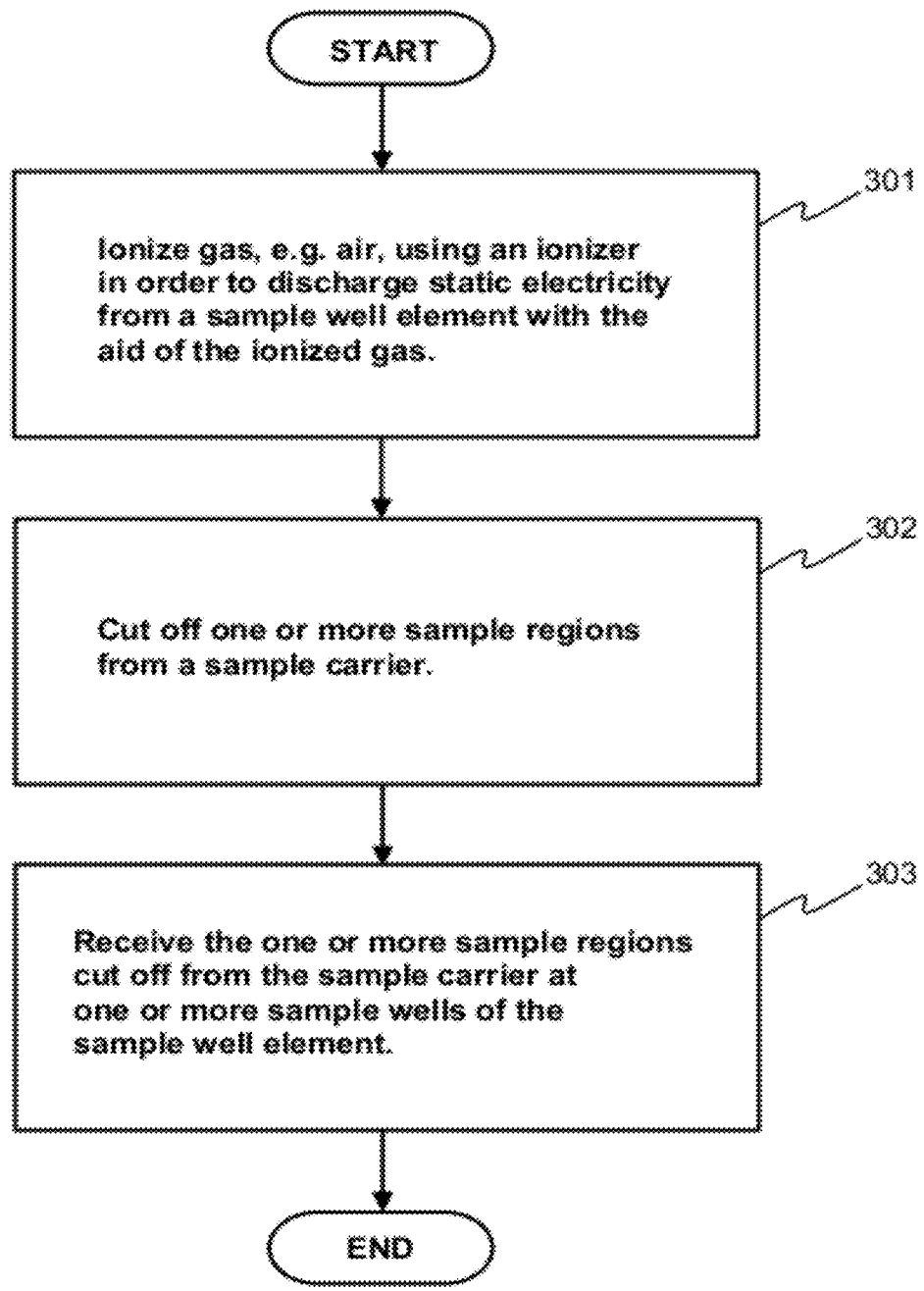
FIG. 3 shows a flow chart of a method according to an exemplifying embodiment of the invention for cutting off one or more sample regions from a sample carrier that contains impregnated sample material.

FIG. 3 shows a flow chart of a method according to an exemplifying embodiment of the invention for cutting off one or more sample regions from a sample carrier that contains impregnated sample material, e.g. blood. The method comprises:

- in the phase 301: ionizing gas, e.g. air, that is in contact with a sample well element using an electrically charged ionizer in order to discharge static electricity from the sample well element with the aid of the ionized gas,
- in the phase 302: cutting off the one or more sample regions from the sample carrier, and
- in the phase 303: receiving the one or more sample regions cut off the sample carrier at one or more sample wells of the sample well element.

The detached one or more sample regions that have been received at the sample wells may be later subjected to e.g. biochemical analysis.

In a method according to an embodiment of the invention, alternating "AC" voltage is connected between the ionizer and a body structure of a device comprising the ionizer.

In a method according to an embodiment of the invention, the ionizer comprises two parts that are electrically insulated from each other and alternating voltage is connected between the two parts of the ionizer.

In a method according to an embodiment of the invention, the frequency of the alternating voltage is on the range 20-200 Hz, and the amplitude of the alternating voltage is on the range 2-10 kV. More advantageously, the amplitude of the alternating voltage can be on the range 5-10 kV.

In a method according to an embodiment of the invention, the ionizer comprises two parts that are electrically insulated from each other and direct "DC" voltage is connected between the two parts of the ionizer.

In a method according to an embodiment of the invention, the ionizer comprises a plurality of sharpened spikes so as to maximize the peak value of the electrical field strength in the vicinity of the ionizer.

In a method according to an embodiment of the invention, the spikes of the ionizer are directed towards openings of the sample wells of the sample well element.

In a method according to an embodiment of the invention, a distance from tips of the spikes to the openings of the sample wells of the sample well element is on the range 1-6 mm.

In a method according to an embodiment of the invention, the spikes are supported with a support made of electrically insulating material so as to minimize capacitance between the ionizer and other parts of the device comprising the ionizer.

In a method according to an embodiment of the invention, the support made of the electrically insulating material is provided with holes and/or cuts in order to decrease a surface area of the support so as to minimize capacitance between the support and other parts of the device comprising the ionizer.

In a method according to an embodiment of the invention, the one or more sample regions are cut off with a punch and a die provided with a channel for the punch, where the punch is capable of cutting off each sample region with a stroke through the sample carrier. A method according to another embodiment of the invention comprises moving a point-form cutting impact produced by a cutting instrument along the outer periphery of each sample region so as to cut off the sample region from the sample carrier. The above-mentioned cutting instrument can be, for example, a laser beam cutter or a liquid jet cutter.

The specific examples provided in the description given above should not be construed as limiting. Therefore, the invention is not limited merely to the embodiments described above.

What is claimed is:

1. A device for cutting off one or more sample regions from a sample carrier that contains impregnated sample material, the device comprising:
   - a cutting unit for cutting off the one or more sample regions from the sample carrier,
   - a support element for supporting a sample well element so that the sample well element is able to receive the one or more sample regions cut off from the sample carrier, and
   - an ionizer for ionizing gas that is, when the sample well element has been placed to the support element, in contact with the sample well element so as to discharge static electricity from the sample well element.

2. A device according to claim 1, wherein the device comprises a voltage source, a first electrical terminal of the voltage source being connected to the ionizer.

3. A device according to claim 2, wherein the voltage source is an alternating voltage source and a second electrical terminal of the voltage source is connected to a body of the device.

4. A device according to claim 3, wherein the frequency of alternating voltage produced by the alternating voltage source is on the range 20-200 Hz, and the amplitude of the alternating voltage is on the range 2-10 kV.

5. A device according claim 2, wherein the ionizer comprises two parts that are electrically insulated from each other and the first electrical terminal of the voltage source is connected to a first part of the ionizer and a second electrical terminal of the voltage source is connected to a second part of the ionizer.

6. A device according to claim 5, wherein the voltage source is a direct voltage source.

7. A device according to claim 2, wherein the voltage source is an alternating voltage source.

8. A device according to claim 1, wherein the ionizer comprises a plurality of sharpened spikes so as to maximize the peak value of electrical field strength in the vicinity of the ionizer.

9. A device according to claim 8, wherein the spikes of the ionizer are directed so that, when the sample well element is in its normal operation position in the support element, the spikes are towards openings of the sample wells of the sample well element.

10. A device according to claim 8, wherein the spikes are mechanically supported with a support made of electrically insulating material so as to minimize capacitance between the ionizer and other parts of the device.

11. A device according to claim 9, wherein a distance from tips of the spikes to a spatial plane that co-insides with a bottom of the sample well element, when the sample well element is in its normal operation position in the support element, is on the range 10-15 mm.

12. A device according to claim 1, wherein the ionizer comprises elongated electrical conductors mechanically supported by a support made of electrically non-conductive material, and a total area of the electrical conductors is at most a tenth of an area of a smallest closed spatial surface capable of enclosing the ionizer so as to minimize capacitance between the ionizer and other parts of the device.

13. A device according to claim 12, wherein the support made of the electrically insulating material is provided with holes and/or cuts in order to decrease a surface area of the support so as to minimize capacitance between the support and other parts of the device.

14. A device according to claim 1, wherein the cutting unit comprises a punch and a die provided with a channel for the punch, the punch being arranged to cut off each sample region with a stroke through the sample carrier.

15. A device according to claim 1, wherein the cutting unit comprises a cutting instrument for producing a point-form cut on the sample carrier and equipment for directing the cutting instrument so that cutting impact produced by the cutting instrument is moved along the outer periphery of each sample region so as to cut off the sample region.

16. A method for cutting off one or more sample regions from a sample carrier that contains impregnated sample material, the method comprising:
cutting off the one or more sample regions from the sample carrier,
receiving the one or more sample regions cut off from the sample carrier at a sample well element, and
prior to cutting off the one or more sample regions, ionizing gas that is in contact with the sample well element using an ionizer in order to discharge static electricity from the sample well element.

17. A method according to claim 16, wherein alternating voltage is connected between the ionizer and a body structure of a device comprising the ionizer.

18. A method according to claim 17, wherein the frequency of the alternating voltage is on the range 20-200 Hz, and the amplitude of the alternating voltage is on the range 2-10 kV.

19. A method according claim 16, wherein the ionizer comprises two parts that are electrically insulated from each other and alternating voltage is connected between the two parts of the ionizer.

20. A method according claim 16, wherein the ionizer comprises two parts that are electrically insulated from each other and direct voltage is connected between the two parts of the ionizer.

21. A method according to claim 16, wherein the ionizer comprises a plurality of sharpened spikes so as to maximize the peak value of electrical field strength in the vicinity of the ionizer.

22. A method according to claim 21, wherein the spikes of the ionizer are directed towards openings of the sample wells of the sample well element.

23. A method according to claim 22, wherein a distance from tips of the spikes to the openings of the sample wells of the sample well element is on the range 1-6 mm.

24. A method according to claim 21, wherein the spikes are supported with a support made of electrically insulating material so as to minimize capacitance between the ionizer and other parts of the device comprising the ionizer.

25. A method according to claim 24, wherein the support made of the electrically insulating material is provided with holes and/or cuts in order to decrease a surface area of the support so as to minimize capacitance between the support and other parts of the device.

26. A method according to claim 16, wherein the one or more sample regions are cut off with a punch and a die provided with a channel for the punch, the punch being capable of cutting off each sample region with a stroke through the sample carrier.

27. A method according to claim 16, wherein the method comprises moving a point-form cutting impact produced by a cutting instrument along the outer periphery of each sample region so as to cut off the sample region from the sample carrier.

* * * * *